United States Patent [19]

Utsumi et al.

[11] 4,005,200
[45] Jan. 25, 1977

[54] METHOD FOR IMPROVING THE MATURITY OF THE PARTURIENT CANAL AND THE SENSITIVITY TO OXYTOCIN

[75] Inventors: Isamu Utsumi, Kyoto; Tomio Endo, Kobe; Tadaaki Kamata, Ibaraki; Masayasu Ando, Takatsuki, all of Japan

[73] Assignee: Kanebo, Ltd., Tokyo, Japan

[22] Filed: July 17, 1975

[21] Appl. No.: 596,741

[52] U.S. Cl. .......................... 424/243; 260/397.5; 424/361
[51] Int. Cl.² ..................................... A61K 31/565
[58] Field of Search .................. 424/242, 243; 260/397.5

[56] References Cited
UNITED STATES PATENTS

| | | | |
|---|---|---|---|
| 2,283,913 | 5/1942 | Butenandt | 260/397.5 |
| 2,567,268 | 9/1951 | Beall | 260/397.5 |
| 3,193,457 | 7/1965 | Kincl | 424/242 |
| 3,743,730 | 7/1973 | Adams | 424/243 |

*Primary Examiner*—Albert T. Meyers
*Assistant Examiner*—Vera C. Clarke
*Attorney, Agent, or Firm*—James C. Haight

[57] ABSTRACT

A new use of dehydroepiandrosterone sulfate or its salt as a parturient canal conditioning agent is disclosed.

The maturity of the parturient canal and the sensitivity of uterine musculature to oxytocin are improved resulting in normal parturition by administering to a pregnant human subject at the 37th to 39th week of pregnancy a therapeutically effective amount of dehydroepiandrosterone sulfate or its pharmaceutically acceptable salts such as the sodium salt.

5 Claims, No Drawings

METHOD FOR IMPROVING THE MATURITY OF THE PARTURIENT CANAL AND THE SENSITIVITY TO OXYTOCIN

This invention relates to a method for improving the maturity of the parturient canal and the sensitivity of uterine musculature to oxytocin. It also relates to a pharmaceutical preparation for use in carrying out the method.

It has been well known that the difficulty of parturition depends upon the expulsion strength and the state of the parturient canal and fetus. The most undeveloped area in the obstetric treatment for improving the state of parturition is in methods to improve the maturity of the parturient canal, particularly the portion including the uterine cavity, cervical and vaginal canals. It would be very advantageous if one could improve the state of the parturient canal for normal birth of the baby by a simple medication.

It has been well known that great quantities of estrogens are formed by placental tissue during pregnancy. The peak production is reached immediately before birth of the baby. The function of estrogens during pregnancy had been explained as follows. They cause enlargement of the external sex organs and of the vaginal opening, providing an appropriately enlarged parturient canal, and they also help to relax the ligaments of the pelvis so that the pelvis opening can stretch as the baby is born.

It has been found that external administration of a large amount of estrogens has substantially no effect in improving maturity of the parturient canal in terms of Bishop's score. Furthermore, the administration of estrogens is not practical because of its delayed reaction, difficulty in selecting an appropriate time for the administration and undesirable side effects.

We have now found that when an effective dose of dehydroepiandrosterone sulfate or its phamaceutically acceptable salt is administered to a pregnant mother in the 37th to 39th week of pregnancy, the maturity of the parturient canal and the sensibility of uterine musculature to oxytocin have been remarkably improved.

It is proposed to call such a drug which can improve the parturient canal for normal parturition the "parturient canal conditioning agent."

Dehydroepiandrosterone sulfate (hereinafter referred to as "DHA-S") has the following structural formula:

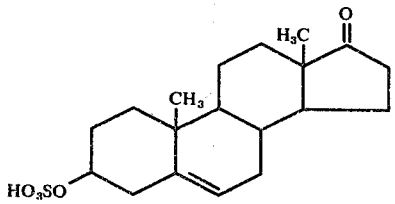

the compound occurs in adrenal glands and is secreted therefrom. In 1963, E. E. Baulieu et at. considered it as a privileged hormonal substance in a new type of endocrine secretion.

It has been proposed to use clinically esters of dehydroepiandrosterone in combination with estrogens in the treatment of various syndromes associated with climacterium. Obviously, this treatment utilizes the androgenic activity of dehydroepiandrosterone which has long been known in the art.

When an effective dose of DHA-S or salts thereof is administered to the pregnant mother at an appropriate time of pregnancy in accordance with the present invention, the level of estrogens in the maternal blood increases rapidly reaching a peak within a few hours. It is postulated that the increased blood level of estrogens caused by the administration of DHA-S may be attributed to the fact that DHA-S is transformed to estrogens by the placental tissue. Thus the administration of DHA-S results in a rapid, remarkable increase of estrogen concentration selectively in the uterine tissue thereby promoting the maturity of the cervix and other parts of the parturient canal. At the same time, the concentration of progesterone secreted by the placenta decreases, which normally must begin a few weeks prior to the birth. This results in increase of the sensitivity of uterine musculature to oxytocic activity and more intense uterine contractions are obtained during the period of labor.

DHA-S usually occurs as the sodium salt but other water-soluble salts, such as potassium salt or ammonium salt, may be used for parental administration in the form of a solution. Free sulfate and water-insoluble salts, such as calcium, magnesium and aluminum salts and the like, may be used for oral administration in the form of tablets, capsules and the like. Parenteral administration, such as intravenous or intramuscular injections, and oral administration are preferable. The dose varies with the state of the particular mother (the maturity of the cervix and sensitivity to oxytocin) and is generally within the range from 10mg. to 1g, preferably from 50mg. to 500mg./ person/pregnancy. The dose may be administered once or divided into several doses over a few days or weeks during the 37th to 39th week of pregnancy.

The effects of DHA-S and its salts on the parturition were tested clinically using the double blind method.

1. Method 1.1 Subject 168 patients 18 to 42 years old in not earlier than the 37th week of pregnancy were chosen. Both parous and new-parous women were included. When the results were studied statistically, they were classified in accordance with the age, weeks of pregnancy, former experience of parturition, presence or absence of a concurrent disease, and periodicity of the menstrual cycles.

1.2 drugs

100mg. of DHA-S sodium salt was used.

As a control drug, a placebo which is indistinguishable from the active drug in appearance was used. Distribution of the drugs to individual patients was carried out at random by a controller who kept the table of the distribution of the drugs.

1.3 Dose and Administration Method

Two vials each containing 50mg. of crystals of DHA-S sodium salt were dissolved 10ml. of aqueous solution of benzyl alcohol and a single dose of the solution was administered intravenously.

1.4 Observation

After the administration, the maturity of uterine cervix of the individual subjects was daily observed in terms of Bishop's score for a week. Similarly the sensibility of uterine musculature to oxytocin was determined by Smyth's method.

Upon parturition, the length of the required time during labor periods I and II, general observation of the labor and the duration of pregnancy between the time of the last menstrual period and the birth of the baby were noted. Also, physiological jaundice, asphyxia and the body weights of the babies were recorded.

1.5 Judgement

After the completion of the tests, all of the data obtained were given to the controller and the distribution table of the durgs was opened. The effect was judged by the statistical treatment of the data for the treated and the control groups.

2. Results

The subjects were divided into the group treated with DHA-S sodium salt and the control group. In each group, significant differences in the distributions were not shown with respect to the ages, former experience of parturition, presence or absence of concurrent diseased, and the periodicity of menstrual cycles.

2.1 Effect of DHA-S on maturity of the uterine cervix.

a. The promoting or maturity of the uterine cervix

One day after the administration of DHA-S, the maturity increased by 47.9%, whereas the corresponding rate with the control group was 34.6%. At 2 days and 3 days after the administration, the DHA-S administered group continued to show a greater increase than that of the control group.

During the 37th to 39th week of pregnancy, the administration of DHA-S increased the maturity by 66.7% at 1 day after the administration in contrast with the rate of 15.8% of the control group (0.05). At 2 days after administration, the DHA-S administered group continued to show a greater increase than that of the control group.

At the 40th week of pregnancy or later, a significant difference in the effect was not seen between the two groups.

In the groups comprising experienced subjects, the DHA-S administered group showed an increasing rate of 50.0% at 1 day after the administration and the control group showed the rate of 10.5%.

The former is significantly higher than the latter, with confidence limits $p < 0.05$.

b. The increase of Bishop's score

The maturity of the uterine cervix was expressed in terms of Bishop's score. Mean values of the increase in the score were calculated with respective groups. At 1 day after the administration, the DHA-S administered group showed the mean value of $1.22 \pm 0.24$ in contrast with the value of $0.51 \pm 0.18$ in the control group. Thus the score of the former group increased about 0.7 points higher than that of the control group ($p < 0.05$). In the 2nd day after the administration, the mean values of the two groups were $1.35 \pm 0.35$ and $0.69 \pm 0.19$, respectively.

The difference between the values of the two groups was about 0.7 and the score of the DHA-S administered group was higher than that of the control group ($0.05 < p < 0.1$).

The administration of DHA-S caused an increase of about 0.9–1.5 points in the Bishop's score within a day, whereas the score in the control group increased only about 0.2–0.6 points within a day.

2.2 Effect of DHA-S on sensitivity to oxytocin

Sensitivity to oxytocin was determined by Smyth's method which has been the most conventional method. According to this method, the patients were laid down and an external tocometer was set. After 15 minutes, a solution of 0.01 I.U. of synthetic oxytocin was administered intravenously at an interval of 1 minute repeatedly. From the readout of the tocometer, it was determined as a positive or negative effect. At 1 day after the administration of the drug, increases in the sensibility to oxytocin were recognized in 27.9% of the group of the subjects administered DHA-S. The corresponding percentage in the control group was 17% which is 10% less than that of the DHA-S administered group.

With the groups off parturition-experienced subjects, the increase was recognized in 46.2% and 10% respectively in the DHA-S administered group and the control group on the next day. Thus the increase in the sensibility to oxytocin was acknowledged within the limits of confidence of $0.05 < p < 0.1$.

In the above tests, the length of the labor periods I and II was slightly shortened in the DHA-S administered group. The administration had no effect on the duration of pregnancy until parturition, general conditions of the parturition or the baby.

Furthermore, DHA-S showed no adverse effect on the mother and the baby.

3. Oral administration 30 subjects with a pregnancy of 37 weeks or more were divdied into two groups. Two tablets each containing 50mg. of DHA-S sodium salt were administered for 3 consecutive days and the results were observed on the 4th day.

Similarly, placebo tablets were administered to the control group according to a double blind method.

The DHA-S administered group showed an increasing rate of 70% on the maturity of uterine cervix while the rate in the control group was 35.7%. The increase of Bishop's score was $1.60 \pm 0.54$ in the DHA-S administered group and $0.36 \pm 0.20$ in the control group respectively ($p < 0.05$). The increase in the sensibility to oxytocin was recognized in 60% of the DHA-S administered group and 23.1% of the control group respectively with a significant difference. Any undesirable side effect was observed with the administration of DHA-S.

Pharmaceutical preparations containing DHA-S may be prepared in a conventional manner by mixing the active ingredient with known excipients.

For parenteral use, the formulations must be sterile and are presented in sealed containers such as ampules, vials and the like. A preferred form is a vial containing a predetermined amount of sterile, crystalline powder of DHA-sodium salt, which is to be dissolved prior to use in 2% aqueous solution of benzyl alcohol, which may be supplied in a separate sealed container under sterile conditions.

The following examples are offered for illustrative purposes only.

Preparation of DHA-S sodium salt

To a 5 capacity flask having a stirrer, thermometer, and a condenser are added 2l. of pyridine and 233g. of sulfamic acid. The mixture is stirred at 70–75° C for 1 hour and then 230g. of dehydroepiandrosterone is added. After stirring at the same temperature for 1 hour, the reaction mixture is cooled to room temperature. To the mixture is added 170g. of anhydrous sodium carbonate in 2l. of water and the mixture is evaporated in vacuo at 40°–45° C until the volume becomes 1l.

After diluting with 1l. of water, the solution is allowed to stand in a refrigerator overnight. The resulting crystals are filtered off and then recrystallized repeatedly, whereby 439g. of DHA-S sodium salt is obtained.

LD50 values of DHA-S sodium salt were determined by LitchfieldWilcoxon's method on the basis of 3 days mortality using mice and rats. The results are shown in the following table.

| Route | LD 50 value of DHA-SNa (mg/kg) | | |
|---|---|---|---|
| | Sex | Mice | Rats |
| PO | | > 9500 | > 9500 |
| SC | | 2520 | 6870 |
| | | 3400 | 4050 |
| IP | | 560 | 1560 |
| | | 605 | 840 |
| IV | | 270 | 460 |
| | | 280 | 480 |

Pharmaceutical Preparations a. Compressed Tablets

| Pharmaceutical Preparations: | | |
|---|---|---|
| a) | Compressed Tablets | |
| | DHA-S Na · 2H$_2$O | 50.0 mg. |
| | lactose | 182.5 mg. |
| | talc | 2.5 mg. |
| | dry potato starch | 12.5 mg. |
| | magnesium stearate | 2.5 mg. |
| | | 250.0 mg. |

Procedure

A mixture of DHA-S sodium salt with lactose and starch is granulated with water and dried. The granules are mixed with talc and magnesium stearate thoroughly and compressed into tablets each weighing 250mg.

b. Coated Tablets

The compressed tablets obtained in the above procedure are coated with an aqueous suspension of sugar, gelatin, gum arabic, calcium carbonate and talc in the usual way.

c. Enteric Coating Tablets

The compressed tablets obtained in the above procedure are coated with a solution of cellulose acetate phthalate, titanium dioxide, acetone and methylene chloride in the usual way.

d. Injectable preparations for parenteral use

Active ingredient

100mg. of DHA-S Na.2H$_2$O prepared under sterile conditions are placed in a vial under sterile conditions. The vial is sealed with a sterile rubber stopper and then covered with an aluminum cap.

Solvents benzyl alcohol 0.1 g.
sterile distilled water 4.9 g. /5.0 g.

The two ingredients are mixed and then placed in a sealed glass ampule. The ampules are sterilized again in the usual way. Two ampules are used to dissolve 1 vial of DHA-S prior to use.

We claim:

1. A method for improving the maturity of parturient canal and the sensibility of uterine musculature to oxytocin, which comprises administering to a living pregnant human a therapeutically effective amount of dehydroepiandrosterone sulfate or a pharmaceutically acceptable salt thereof at the 37th to 39th week of pregnancy.

2. The method according to claim 1, wherein dehydroepiandrosterone sulfate sodium salt is administered.

3. The method according to claim 2, wherein dehydroepiandrosterone sulfate sodium salt is administered at a dose of 50mg. to 500mg.

4. The method according to claim 2, wherein the sodium salt is administered orally.

5. The method according to claim 2, wherein the sodium salt is administered parenterally.

* * * * *